(12) United States Patent
Romine

(10) Patent No.: US 7,213,604 B2
(45) Date of Patent: May 8, 2007

(54) DENTAL FLOSSING TOOL AND DISPENSER

(75) Inventor: William R. Romine, Spokane, WA (US)

(73) Assignee: Advanced Floss Systems, L.L.C., Spokane, WA (US)

( * ) Notice: Subject to any disclaimer, the term of this patent is extended or adjusted under 35 U.S.C. 154(b) by 378 days.

(21) Appl. No.: 10/858,451

(22) Filed: Jun. 1, 2004

(65) Prior Publication Data
US 2005/0263169 A1    Dec. 1, 2005

(51) Int. Cl.
*A61C 15/00* (2006.01)
(52) U.S. Cl. ...................................... 132/325
(58) Field of Classification Search ................ 132/324, 132/325, 326
See application file for complete search history.

(56) References Cited

U.S. PATENT DOCUMENTS

| | | | |
|---|---|---|---|
| 2,098,610 A | 11/1937 | Bluhm | |
| 2,381,530 A | 8/1945 | Dembenski | |
| 3,340,881 A | 9/1967 | Cowan | |
| 3,746,017 A * | 7/1973 | Casselman | 132/325 |
| 3,927,687 A * | 12/1975 | Thierman | 132/325 |
| 4,326,549 A | 4/1982 | Hinding | |
| 4,518,000 A * | 5/1985 | Leverette | 132/325 |
| 4,550,741 A | 11/1985 | Krag | |
| 5,160,077 A | 11/1992 | Sticklin | |
| 5,269,331 A * | 12/1993 | Tanriverdi | 132/325 |
| 5,495,863 A | 3/1996 | Bergman | |
| 5,823,207 A * | 10/1998 | Bushman | 132/323 |
| 6,253,774 B1 | 7/2001 | Mason | |
| 6,295,996 B1 | 10/2001 | Dickle | |

* cited by examiner

*Primary Examiner*—Todd E. Manahan
(74) *Attorney, Agent, or Firm*—Reidlaw, L.L.C.; John S. Reid

(57) ABSTRACT

A dental flossing tool and dispenser includes a case with an enclosed chamber divided by a partition wall into floss spool and take up reel compartments. A hub mounts a floss spool for rotation within the floss spool compartment. A take up reel is rotatable within the take up reel compartment. A rotator on the take up reel, is at least partially disposed outward of the take up reel compartment. Floss in-feed and out-feed openings in the case communicate with the respective compartments. A length of floss extends through the floss out-feed opening and back into the take up reel compartment through the floss in-feed opening, thereby forming a bight in the floss outward of the case. A unidirectional rotation limiter allows rotation of the take up reel to take up the length of floss but inhibits pay out of floss.

19 Claims, 4 Drawing Sheets

DENTAL FLOSSING TOOL AND DISPENSER

FIELD OF THE INVENTION

The invention claimed and disclosed herein pertains generally to dental flossing and more particularly to a flossing tool and dispenser that facilitates dental flossing procedures.

BACKGROUND

Dental flossing has long been advised by those in the dental field as a way to reduce the number of bacteria between teeth that might cause decay; to prevent plaque build-up and avoid periodontal and other tooth and gum related diseases. While daily flossing is recommended at a minimum, some prefer flossing after meals and carry floss about for that purpose.

The typical floss dispenser carries a roll of floss within a small plastic box. Floss is pulled from the box and is trimmed on a cutting device supplied on the box. The cut length of floss is then wound about a finger on each hand so a length of floss connects the two fingers. The floss is drawn taut between the fingers and the taut span is inserted in the mouth and the fingers are worked to force the floss into the interstices between adjacent teeth. The floss is then moved back and forth between the teeth to clean the engaged surfaces. After several strokes, the floss is pulled out and the process is repeated on the next pair of teeth. It is not unusual to use more than a foot of floss in a single flossing procedure.

A person who has finished the above described operation is left with a length of unsanitary and unsightly floss to dispose of. While disposing of used floss is not always a challenge, it is in circumstances where a proper disposal receptacle is not available.

Standard forms of flossing tools typically involve the use of a rigid or semi-rigid elongated handle, which, in many such tools has a forked end. Floss is drawn taut between the bifurcations. The use of short lengths of floss with such tools is more economical than hand application, which can easily consume twelve or more inches of floss per use. However, the forks or other floss holders do not permit the tactile capability that is available during hand flossing, and the dispensing problem discussed above can remain a problem. Further, flossing tools that must be inserted into the mouth become unsanitary unless they are cleaned after each use.

While some flossing tools accommodate used floss on separate spools, hygiene is still a problem because contaminated used floss is not adequately separated from the fresh, unused floss.

SUMMARY

One embodiment of the invention provides for a dental flossing tool and dispenser in which a case defines an enclosed chamber. A partition wall separates the chamber into a floss spool compartment and a take up reel compartment. A hub is located within the floss spool compartment and a spool of floss is mounted on the hub. A take up reel is mounted for rotation in the take up reel compartment. A rotator is connected to the take up reel and is disposed at least partially outward of the take up reel compartment. Floss in-feed and out-feed openings are formed in the case, communicating respectively with the take up reel compartment and the floss spool compartment. A length of floss is wound on the floss spool and extends outwardly through the floss out-feed opening and back into the take up reel compartment through the floss in-feed opening to connect with the take up reel, thereby forming a bight in the floss outward of the case. A unidirectional rotation limiter is connected to the rotator and operates to allow rotation of the take up reel to take up the length of floss and to inhibit rotation of the take up reel to pay out floss.

In another aspect, the invention includes a dental flossing tool and dispenser in which a case provides a partition wall, separating the chamber into a floss spool compartment and a take up reel compartment. A floss spool has a length of floss wound thereon and a hub mounts the floss spool within the floss spool compartment for rotation about a spool axis. An out-feed motion limiter is configured to normally inhibit the floss and hub from rotating to pay out floss from the spool of floss. An actuator is movably mounted to the case and is selectively operable to shift the out-feed motion limiter to allow rotation of the hub and floss spool to pay out floss from the floss spool. A take up reel is mounted in the take up reel compartment for rotation about a take up reel axis, and a rotator is connected to the take up reel and disposed outward of the take up reel compartment. A unidirectional rotation limiter is connected to the rotator and operable to allow rotation of the take up reel to take up the length of floss and to inhibit rotation of the take up reel to pay out floss. A floss out-feed opening is located in the case, communicating with the floss spool compartment, and a floss in-feed opening in the case, communicating with the take up reel compartment. A length of floss from the floss spool extends outwardly from the floss spool through the floss out-feed opening and back into the take up reel compartment through the floss in-feed opening to connect with the take up reel, thereby forming a bight in the floss, outward of the case.

A further aspect of the invention includes a dental flossing tool and dispenser in which a case is formed of hard plastic and shaped to fit within a human hand, the case being hollow and forming an interior chamber that is divided by a partition wall into a substantially sealed floss spool compartment and a take up reel compartment. A floss out-feed opening is disposed on one side of the case, adjacent to the partition wall and communicating with the floss spool compartment. A floss in-feed opening is formed in the one side of the case, adjacent to the partition wall and communicating with the take up reel compartment. A length of floss extends from a spool in the floss spool compartment, out through the floss out feed opening, and back through the floss in-feed opening into the take up reel compartment; thereby forming a bight of floss outward of the case. Raised surfaces on the one side of the case, are spaced apart between the floss in-feed opening and the floss out-feed opening to engage and hold the bight of floss clear of the case and allow finger access thereto. An out-feed motion limiter operably engages the spool to normally inhibit out-feed of floss through the out-feed opening. A hand operated actuator is positioned on the case in opposition to the in-feed and out-feed openings, and moves thereon to release the spool and allow floss to be drawn from the spool through the out-feed opening.

The above and further aspects and embodiments will next be described in detail with reference to the accompanying drawings which, taken along with the following detailed description and claims, disclose the best mode presently known for carrying out the invention.

DETAILED DESCRIPTION

Embodiments of the present invention provide for a compact hand held floss dispenser that does not require positioning of the floss holder within the user's mouth, and that will permit conservation of floss, while allowing hand flossing. The present invention also provides for a flossing tool in which used floss can be collected and maintained separate from fresh, unused floss. The present invention further avoids the shortcomings and detriments associated with prior art dental floss devices.

Figure 1:
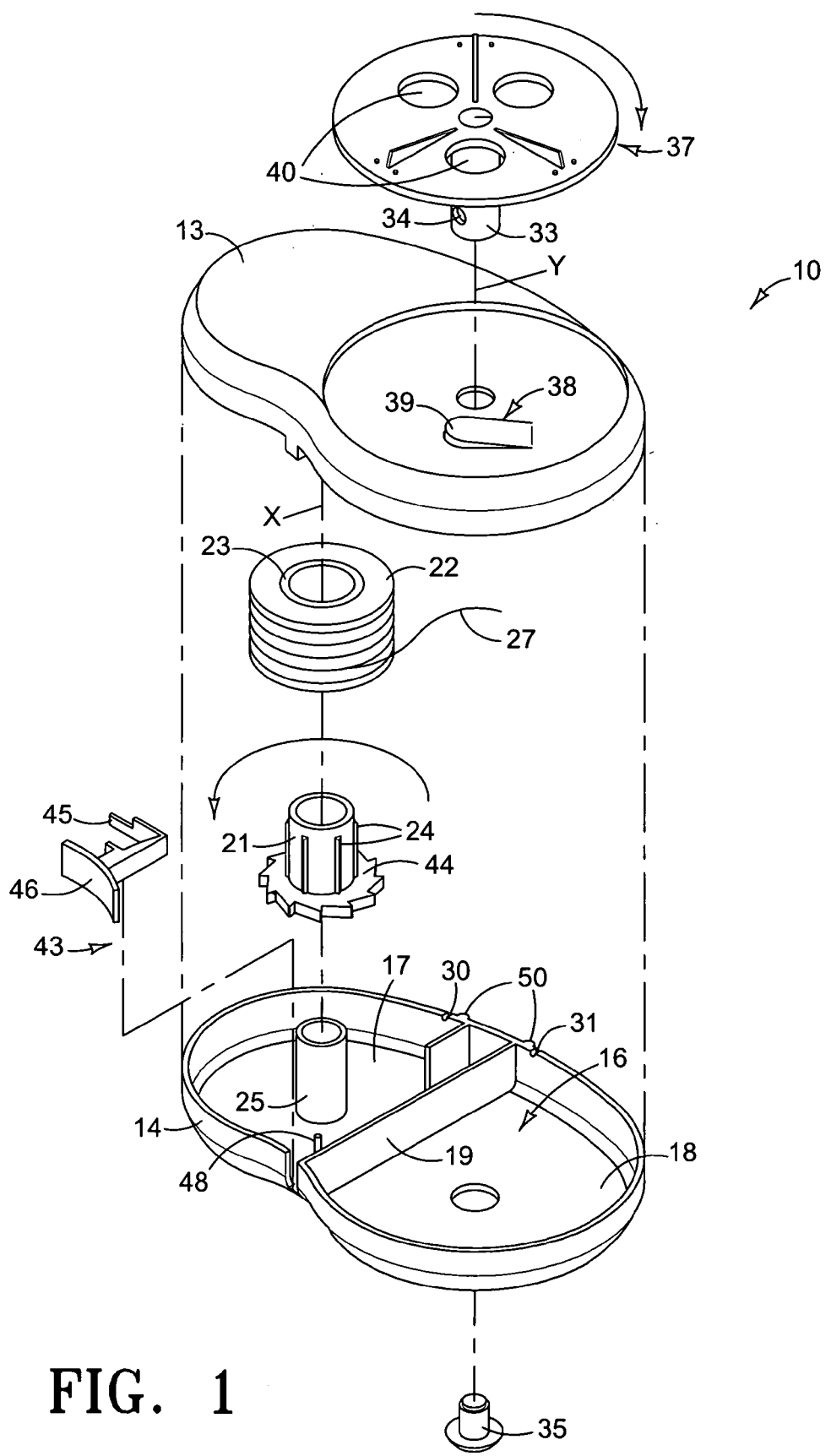
FIG. 1 is an exploded perspective view of an embodiment of the present invention.
Figure 2:
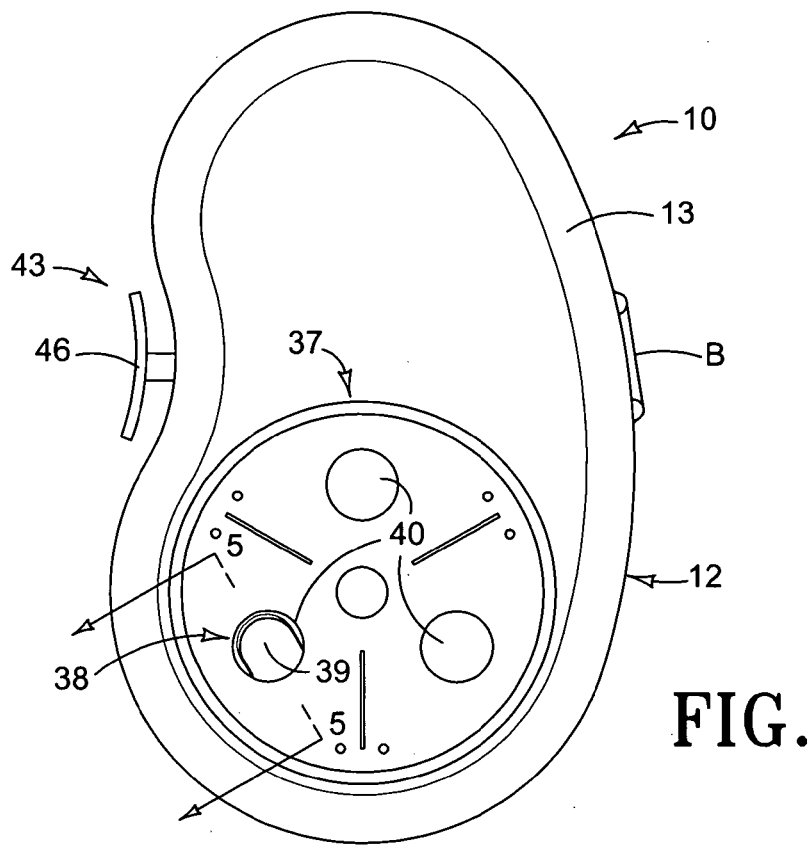
FIG. 2 is a top plan view of an assembled unit.

Looking now to the drawings in greater detail, with attention first drawn to FIGS. 1 and 2, an embodiment of the present flossing tool and dispenser is identified by the reference numeral 10. The tool 10 is shown in FIG. 1 in exploded view, and assembled in FIG. 2. The remaining figures show various aspects of the tool 10 in fragmented or sectional views.

In overall configuration, the exemplified tool and dispenser 10 is of a kidney shape, similar in size to a conventional rectangular dental floss box. The compact size allows for ease in carrying in a pocket or purse. While other configurations can be used, the illustrated rounded shape is functionally convenient to the user's hand while preparing the contained floss for use, and is aesthetically pleasing in appearance.

It is pointed out that all embodiments in accordance with the present invention share aspects that are common and which will therefore be assigned like reference numerals, and description of common features of one embodiment will suffice for description of others in order to avoid undue repetition.

The tool 10 includes a case 12 that can be formed of injection molded plastic such as polycarbonate. I have found such plastic to be sufficiently rigid to form the case 12, yet with resiliency to enable use of integral parts of the case as spring biased components that will be described later on in this specification. Polycarbonate is also suitable for sonic welding and can be obtained in different colors and a range of opacity, from opaque to substantially transparent.

Figure 3:
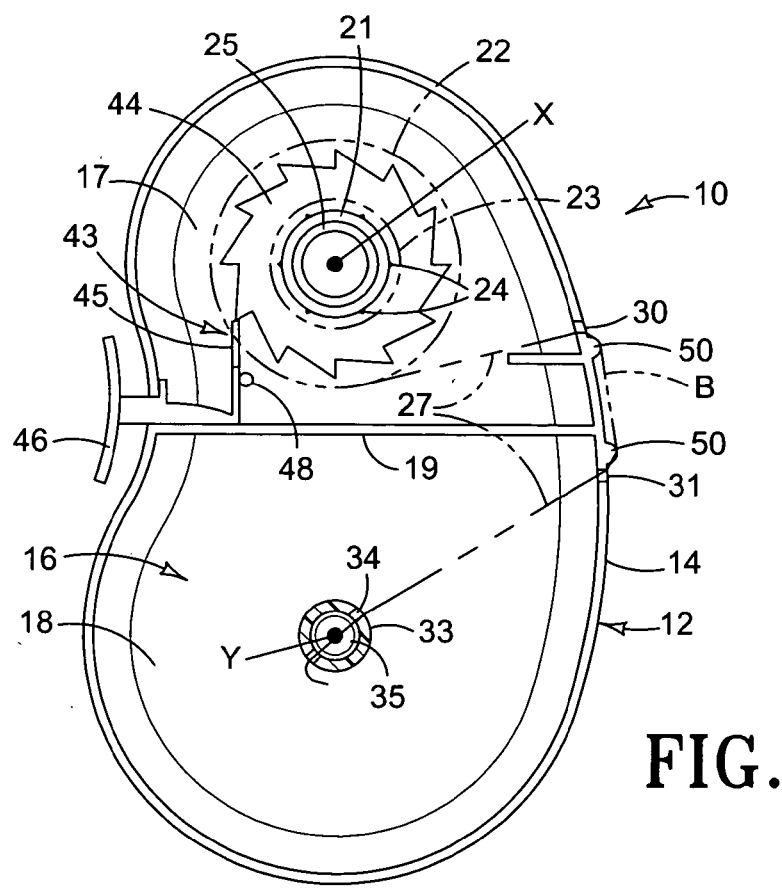
FIG. 3 is a view of a bottom half of the assembled unit with a top case part removed and a floss spool shown in dashed lines.
Figure 4:
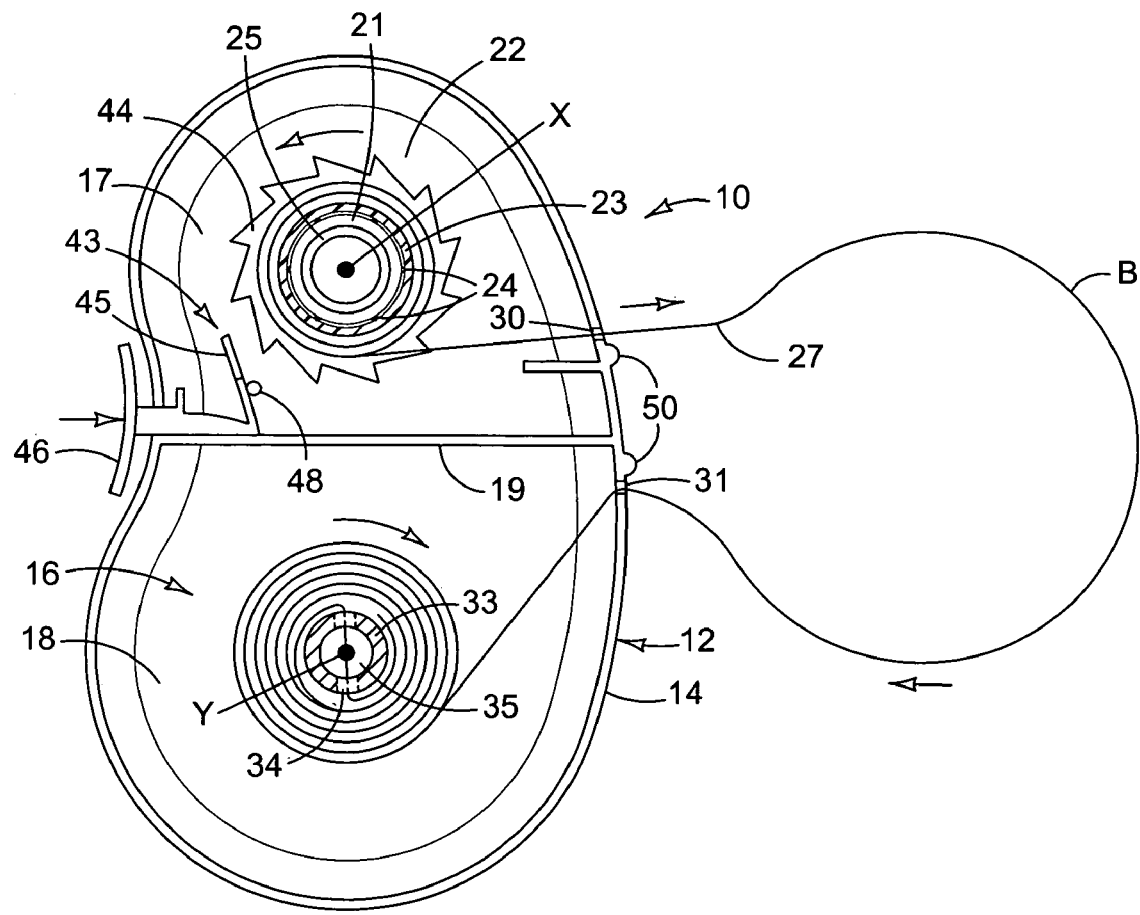
FIG. 4 is a view similar to FIG. 3 only showing a different operational orientation of components and with the floss spool shown in full lines and partially depleted.

The case 12 can be provided in two half sections, a top half 13 and a bottom half 14 (FIG. 1). The case halves 13, 14 can be assembled and sonic welded or otherwise secured together to form a hollow interior chamber 16 that, in turn, is divided into a floss compartment 17 and a take up reel compartment 18 (FIGS. 3, 4).

In the illustrated example, an internal partition 19 separates the chamber 16 into the two compartments 17 and 18. The partition 19 can be formed integrally with one or both of the halves 13, 14 and can also be sonic welded or otherwise secured, as are the case halves 13 and 14. The partition 19 can thus substantially seal the compartments 17, 18 from one another so contaminants from used floss in the take up reel compartment 18 cannot reach the fresh uncontaminated floss in the floss compartment 17.

The floss compartment 17 as illustrated, mounts a hub 21 (FIG. 1) that releasably receives a spool of floss 22. The floss spool 22 can be of a conventional form and can include a tubular central core 23 that can be pressed over the hub 21 which for this purpose, has small longitudinal splines 24 arranged about its perimeter (FIG. 1) in order to substantially lock the spool 22 and hub 21 against relative rotation.

The spool 22 and hub 21 are depicted as being to fit over a post 25 that is formed as an integral part of the bottom case half 14 (FIG. 1). It is pointed out, however, that the post 25 can as well be provided on the top case half 13, or be separately mounted to either case half 13 or 14. The post 25 can be provided as shown in FIGS. 1, 3 and 4, positioned to rotatably receive the hub 21 and spool 22, and defining a rotational spool axis "X" about which the floss spool 22 and hub 21 are selectively allowed to rotate.

A length of floss 27 (FIGS. 3 and 4) can be extended from the floss spool 22, out through a floss out-feed opening 30 that is formed in the case 12, then back into the take up reel compartment 18 through an in-feed opening 31. The part of floss 27 that is exposed outward of the case 12 can be defined as a bight "B" (FIG. 4) and can be made to a size as determined by the user through use of components described below.

Looking at FIGS. 1 and 3, one can see an illustrated example of a take up reel 33 which can be rotatably mounted within the take up reel compartment 18 about a rotational axis "Y". It is noted that in the illustrated embodiments, the axis Y is shown to be substantially parallel to and offset from the spool axis X. This is done to minimize the thickness dimension of the case 12 along the axes X and Y, and to orient the length of floss 27 so it can be fed out and taken up in a plane that is substantially perpendicular to the to the axes X, Y. With this arrangement, floss can be pulled substantially radially from the spool 22 and fed substantially radially onto the take up reel 33.

The take up reel 33 can receive floss through a floss threading hole 34 that can be formed through the case 12, and through which the loose end of the floss length 27 can be threaded. A keeper pin 35 as depicted in FIG. 1, can be received within a hollow end of the take up reel 33 to secure the take up reel 33 with respect to the case 12, and to secure the floss 27 by crimping, against internal surfaces of the take up reel 33. With the floss 27 thus secured, the take up reel 33 can be rotated to wind up the length of bight B, thus changing the size of the bight from a configuration similar to that shown in FIG. 4, to the shortened taut condition shown in FIGS. 2 and 3. The used floss of the bight B can simply be drawn inwardly through the in-feed opening 31, and will wind onto the take up reel 33 as it is rotated. Used sections of the dental floss can be collected in this manner within the take up reel compartment 18.

In order to facilitate rotation of the take up reel 33, a thumb wheel rotator 37 can be provided (FIGS. 1, 2). In the illustrated example, the rotator 37 is disk shaped and provided as an integral part of the take up reel 33. Rotation of the rotator 37 will thus directly effect rotation of the take up reel 33. While other relationships can be used in place of the integral rotator 37, for example a friction wheel or gear arrangement contacting the take up reel 33, the integrated take up reel 33 and rotator 37 have been found to function well and provide the additional benefit of minimizing production complexity and expense.

In the illustrated example, the rotator 37 is inset slightly within the external surface of the case 12 (FIG. 1), in opposition to the keeper pin 35. This keeps the profile of the rotator 37 minimal with respect to the thickness dimension of the case 12, and reduces the chance that the rotator 37 will snag on articles or clothing within a purse or pocket.

Figure 5:
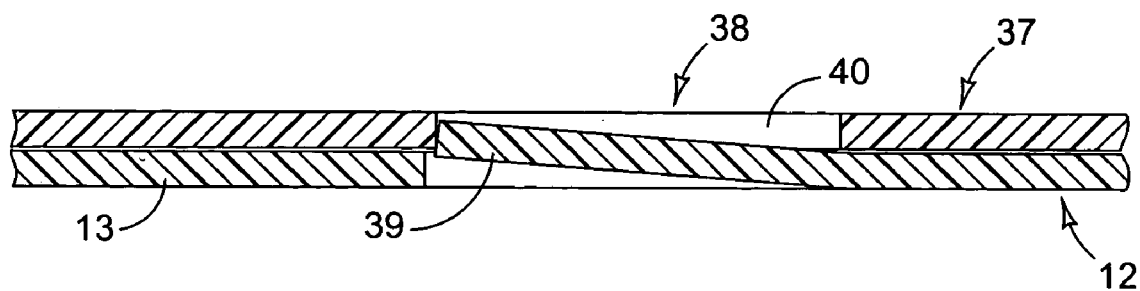
FIG. 5 is an enlarged fragmented sectional view taken substantially along line 5—5 in FIG. 2.
Figure 6:
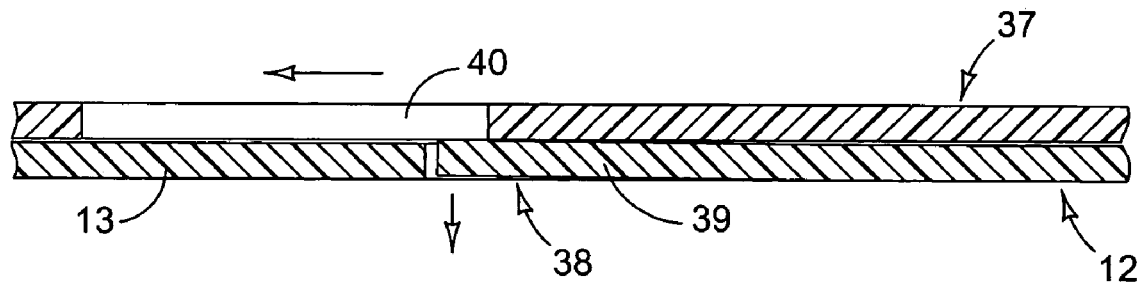
FIG. 6 is a view similar to FIG. 5 only showing a different operational orientation of components.

FIGS. 1, 2, and the detailed fragmentary views in FIGS. 5 and 6, illustrate an exemplary unidirectional motion limiter 38 that can be used to at least inhibit, or to allow only unidirectional rotation for, the take up reel 33. Thus in one embodiment the take up reel 33 can be rotated in one direction only to take up used floss, but cannot rotate to allow the used floss to be pulled back out of the case 12. This is a sanitary consideration that allows for clean, fast take up and storage of used floss lengths (bights B) within the case 12, and without requiring a separate disposal facility.

An exemplary simple and effective construction of the unidirectional motion limiter 38 includes an upwardly sprung tab or pawl 39 (FIGS. 1, 2, 5, and 6) that can be formed as an integral part of the case 12. The pawl 39 can be disposed on the case 12, under the thumb wheel rotator 37 to pop up into successive access openings 40 that can be formed in the rotator 37 at equal radial spacing from the take up reel axis Y. The access openings 40 can have dual functions: to interact with the pawl 39 in providing unidirectional rotation control, and to provide finger or thumb recesses that can be useful when winding the used floss onto the take up reel 33. FIGS. 5 and 6 show in sequence how the pawl 39 springs downwardly and slides under the rotator 37 (as depicted in FIG. 6) until the next successive access opening 40 rotates into position (as depicted in FIG. 5), at which time the pawl 39 snaps upwardly into the presently aligned opening 40 to engage the rotator 37 and prevent rotation in an opposite direction.

It is pointed out that other forms of the unidirectional motion limiter 38 can also be used and still come under the scope of this application. A ratchet wheel, for example, or splined hub can be used in conjunction with a radially biased pawl (not shown). An appropriate friction fit between the case 12 and take up reel 33 can also be used to inhibit undesired rotation of the reel. However the limiter configuration described above allows for a positive unidirectional rotation that allows substantially free rotation in one direction and a reliable lock against rotation in an opposite direction, all with a minimal number of parts.

Control can also be provided to limit directional movement of floss from the spool 22. In the example illustrated, an outfeed motion limiter 43 (FIGS. 1, 3, and 4) can be provided to normally inhibit or, as depicted, prevent rotation of the spool 22 to feed out floss 27. This is done so that floss 27 cannot be unintentionally withdrawn from the spool 22, and so that the bight B is secured. That is to say, once a bight B such as illustrated in FIG. 4 is formed, the outfeed motion limiter 43 can effectively lock the spool 22 against more floss being pulled out from the case 12. Thus the bight B can be effectively secured, with the case 12 becoming part of a formed loop. The floss in the bight B can thus be pulled taut without concern that more floss will be pulled from the spool 22.

Referring to FIGS. 1, 3 and 4, an illustrated example of the outfeed motion limiter 43 is shown comprising a ratchet wheel 44 that is integral or otherwise secured to the hub 21. A pawl 45 in this example is movably mounted within the case and is normally biased to engage the ratchet wheel 44, to effectively prevent rotation of the wheel 44. In the same example, the pawl 45 is integrated with a manually operable actuator, or plunger 46 which extends outward of the case and which is configured to be pressed by the finger or thumb of a user. In response to such action, the pawl 45 is pressed against an abutment 48 that is located within the case (see FIG. 4) and is bent outwardly, disengaging the ratchet wheel 44. To this end, the pawl 45 and plunger 46 can be constructed of a resilient plastic material such as "Celcon" brand polypropylene.

It is noted that the illustrated plunger 46, as depicted in FIGS. 3 and 4, can be slidably mounted to the case 12 and can be guided in backward and forward motion by the case 12 and a portion of the partition wall 19. The case 12 and wall 19 can be employed to slidably guide the plunger 46 in translational motion toward and away from the abutment 48, while the resilient pawl 45 operates against the abutment 48 to normally urge the plunger 46 to its outward position (FIG. 3). Thus, when the plunger 46 is depressed, the pawl 45 will yield (FIG. 4) and bend away from engagement with the ratchet wheel 44, thereby allowing the spool 22 to rotate and pay out floss through the out-feed opening 30. Later, when the plunger 46 is released, the naturally resilient pawl will straighten against the abutment 48 and re-engage the ratchet wheel (FIG. 3) and at the same time, push the plunger 46 back out to its extended position.

It is pointed out that the outfeed motion limiter 43 can be provided in other forms, and, in fact can also be an arrangement by which rotation of the spool is inhibited rather than positively locked against unintentional rotation. This can be done using a friction fit between the post 25 and hub 21. Further, another different form of mechanical linkage arrangement, such as an ordinary one way clutch (not shown) can also be used as equivalent to the ratchet mechanism shown and described below.

Looking now to FIGS. 2–4, the depicted embodiment of the present dental flossing tool and dispenser 10 is shown to include a pair of raised surfaces 50 on the case 12. In the illustrated example, the surfaces 50 are situated between the out-feed opening 30 and the in-feed opening 31 (see FIG. 3 specifically). The surfaces 50, as depicted, function to hold the floss outward of the case 12 (see FIGS. 2 and 3). The small space between the case 12 and floss bight B allows for finger access such that a user can grasp and pull on the floss to create a larger bight B during operation.

Operation of the illustrated forms of the invention may now be easily understood, given the above description of exemplary components. Such description will begin with the tool in the condition illustrated in FIG. 2, with the floss drawn taut between the raised surfaces 50.

To begin use, the user can grasp the case 12 between the first two fingers and thumb. The grip may be such that the two fingers grasp the case at locations outwardly adjacent to the raised surfaces 50, and such that the thumb engages the plunger 46. The thumb can thus be used to depress the plunger 46 and release the outfeed motion limiter 43 so floss can be drawn outwardly from the spool 22 to increase the size of bight B. With the plunger 46 depressed, the user can grasp the exposed floss 27 between the raised surfaces 50 and pull outwardly. The spool 22, which is now released to rotate, will allow floss to be unwound and be drawn outwardly through the out-feed opening 30, forming an enlarged bight B such as illustrated in FIG. 4. When a sufficient amount of floss is withdrawn (usually no more than about six inches is sufficient), the user can release the plunger 46, allowing the pawl 45 to once again engage the ratchet wheel 44 and lock the spool 22 against further rotation.

Next the user is able to floss his or her teeth with the exposed bight B of floss, without need for the case 12 to be inserted into the mouth and without requiring that the user tightly wrap the floss about his or her fingertips. Flossing can be accomplished safely and quickly using just the short amount of floss. The case can be allowed to dangle from the bight B, or be lightly held in either hand. However in either situation, no part of the case 12 is required to be inserted into the user's mouth.

Once the flossing task is finished, the soiled length of floss can quickly and safely be drawn into the case 12, so the user has no need to cut or break the floss, and the contaminated floss can be quickly taken up into the take up reel compartment 18. This can be accomplished by placing a fingertip into one of the access openings 40 in the rotator 37, and revolving the rotator in a motion similar to that used with old style dial telephones. The take up reel 33 will rotate and draw the used floss through the in-feed opening 31 and onto the take up reel compartment 18 where it is isolated from the floss compartment 17. Thus there is little chance for cross contamination of the floss spool held within the floss compartment 17.

As the used floss is wound onto the take up reel, the bight B will grow smaller until such time that it will once again grow taut between the two raised surfaces as depicted in FIG. 2. The unidirectional motion limiter 38 will function as the rotator 37 is turned, to prevent rotation of the take up reel 33 in an opposite direction. Thus the floss 27 can be collected permanently within the relatively sealed take up reel compartment 18, and the remaining unused part of the bight B can be drawn taut between the raised surfaces 50. The floss now forming the bight B can remain in the taut condition, between the raised surfaces 50, until such time that the plunger is once again pressed to release the spool 22 to rotate and pay out additional floss for a subsequent flossing procedure.

The above steps can be repeated until such time that the length of floss on the spool 22 is depleted. Such a state is illustrated in FIG. 3 where the spool is shown partially depleted, and the corresponding amount of used floss is shown on the take-up reel 33. Finally, when the floss is completely depleted from the spool 22, the entire unit can be discarded.

While the above invention has been described in language more or less specific as to structural and methodical features, it is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A dental flossing tool and dispenser, comprising:
   a case forming an enclosed chamber;
   a partition wall separating the chamber into a floss spool compartment and a take up reel compartment;
   a hub within the floss spool compartment;
   a floss spool on the hub;
   a take up reel, rotatable in the take up reel compartment;
   a rotator connected to the take up reel and at least partially disposed outward of the take up reel compartment;
   a floss out-feed opening in the case, communicating with the floss spool compartment;
   a floss in-feed opening in the case, communicating with the take up reel compartment;
   a length of floss wound on the floss spool and extending outwardly through the floss out-feed opening and back into the take up reel compartment through the floss in-feed opening to connect with the take up reel, forming a bight in the floss outward of the case;
   a unidirectional motion limiter comprising a thumb wheel connected to the take up reel, and a biased pawl formed as part of the case and which protrudes outwardly from the case and is configured to slidably and yieldably engage the thumb wheel, to thereby allow rotation of the take up reel to take up the length of floss and to inhibit rotation of the take up reel to pay out floss.

2. The flossing and tool dispenser of claim 1, further comprising an out-feed motion limiter connected to the hub and which is configured to normally at least substantially secure the hub against rotation and thereby inhibit floss from being paid out from the floss spool.

3. The flossing and tool dispenser of claim 1, further comprising an out-feed motion limiter connected to the hub and which is configured to normally lock the hub against rotation and thereby prevent floss from being paid out from the floss spool.

4. The flossing and tool dispenser of claim 3, and wherein the out-feed motion limiter comprises a plunger movably mounted to the case and operable to disengage the hub to permit rotation and allow floss to be paid out from the floss spool.

5. The flossing and tool dispenser of claim 1 wherein the partition wall is configured to substantially seal the floss spool compartment from the take up reel compartment.

6. The dental flossing tool and dispenser of claim 1, and wherein the thumb wheel is exposed outwardly of the case.

7. The dental flossing tool and dispenser of claim 1, wherein:
   the thumb wheel includes thumb wheel access openings; and
   the the biased pawl is configured to snap into the thumb wheel access openings in response to rotation of the thumb wheel in one rotational direction and to engage the thumb wheel through one of the access openings to prevent rotation in a direction opposite to the one rotational direction.

8. The dental flossing tool and dispenser of claim 1, further comprising an out-feed motion limiter connected to the hub and comprised of:
   a ratchet wheel on the hub;
   a pawl positioned to releasably engage the ratchet wheel, and wherein the pawl is biased to normally hold the ratchet wheel, hub and spool of floss against rotation; and
   a plunger movably mounted to the case and configured to move the pawl clear of the ratchet wheel and thereby release the ratchet wheel, hub, and spool of floss to rotate such that floss on the spool can be paid out through the floss out-feed opening.

9. The flossing tool and dispenser of claim 1, further comprising an out-feed motion limiter that includes a ratchet wheel on the hub, and further comprising a plunger movably mounted to the case for movement toward and away from the ratchet wheel and having a flexible pawl positioned to normally engage the ratchet wheel, to prevent rotation of the floss spool to pay out floss therefrom; and further comprising an abutment in the case positioned adjacent to the pawl to bend the pawl away from engagement with the ratchet wheel in response to motion of the plunger toward the floss spool.

10. The flossing tool and dispenser of claim 1, wherein the case is formed in joined halves.

11. The flossing tool and dispenser of claim 1, further comprising raised surfaces on the case, spaced apart between the floss in-feed opening and the floss out-feed opening to hold the floss clear of the case and allow finger access to the bight of floss outward of the case.

12. A dental flossing tool and dispenser, comprising:
a case forming an enclosed chamber;
a partition wall within the case, separating the chamber into a floss spool compartment and a take up reel compartment;
a floss spool having a length of floss wound thereon;
a hub mounting the floss spool within the floss spool compartment for rotation about a spool axis;
an out-feed motion limiter configured to inhibit the floss spool and hub from rotating to pay out floss from the floss spool;
an actuator movably mounted to the case and selectively operable to shift the out-feed motion limiter to allow rotation of the hub and floss spool to pay out a length of the floss from the floss spool;
a take up reel mounted in the take up reel compartment for rotation about a take up reel axis;
a rotator connected to the take up reel and disposed at least partially outward of the take up reel compartment;
a unidirectional motion limiter comprising a thumb wheel connected to the take up reel, and a biased pawl formed as part of the case and which protrudes outwardly from the case and is configured to slidably and yieldably engage the thumb wheel, to thereby allow rotation of the take up reel to take up the length of floss and to inhibit rotation of the take up reel to pay out floss;
a floss out-feed opening in the case, communicating with the floss spool compartment;
a floss in-feed opening in the case, communicating with the take up reel compartment; and
wherein the length of floss from the floss spool extends outwardly from the floss spool, through the floss out-feed opening and back into the take up reel compartment through the floss in-feed opening, thereby forming a bight in the floss, outward of the case.

13. The dental flossing tool and dispenser of claim 12, wherein the spool axis and take up reel axis are spaced apart and substantially parallel.

14. The dental flossing tool and dispenser of claim 12, wherein the out-feed motion limiter includes a ratchet wheel on the hub and a pawl mounted to the case and normally biased against the ratchet wheel to prevent rotation of the hub in one direction.

15. The dental flossing tool and dispenser of claim 12, wherein the actuator includes a manually operable plunger, slidably mounted to the case.

16. The dental flossing tool and dispenser of claim 12, wherein the actuator includes a manually operable plunger that is slidably mounted to the case.

17. The dental flossing tool and dispenser of claim 12, wherein the out-feed motion limiter is comprised of a pawl mounted within the case and biased against the hub to normally inhibit hub rotation in one direction, and wherein the actuator is configured to selectively shift the pawl to a release position in which the pawl is shifted to allow rotation of the hub.

18. A dental flossing tool and dispenser, comprising:
a case formed of hard plastic and shaped to fit within a human hand, the case being hollow and forming an interior chamber that is divided by a partition wall into a substantially sealed floss spool compartment and a take up reel compartment;
a floss out-feed opening on one side of the case, positioned adjacent to the partition wall and communicating with the floss spool compartment;
a floss in-feed opening in the one side of the case, positioned adjacent to the partition wall and communicating with the take up reel compartment;
a length of floss extending from a spool in the floss spool compartment, out through the floss out feed opening, and back through the floss in-feed opening and into the take up reel compartment, thereby forming a bight of floss outward of the case;
raised surfaces on the one side of the case, spaced apart between the floss in-feed opening and the floss out-feed opening to engage and hold the bight of floss clear of the case and allow finger access thereto;
an out-feed motion limiter operably engaging the spool to normally inhibit out-feed of floss through the out-feed opening; and
a hand operated actuator on the case and positioned thereon in opposition to the in-feed and out-feed openings, and movable thereon to release the spool and allow floss to be drawn from the spool through the out-feed opening.

19. The dental flossing tool and dispenser of claim 18, wherein the actuator includes a manually operable plunger that is slidably mounted to the case.

* * * * *